United States Patent [19]

Lee et al.

[11] Patent Number: 5,763,092
[45] Date of Patent: Jun. 9, 1998

[54] HYDROXYAPATITE COATINGS AND A METHOD OF THEIR MANUFACTURE

[75] Inventors: Dusuk Duke Lee, Brookline; William T. Conner, Somerville, both of Mass.

[73] Assignee: Etex Corporation, Cambridge, Mass.

[21] Appl. No.: 582,028

[22] Filed: Jan. 2, 1996

Related U.S. Application Data

[63] Continuation of Ser. No. 121,792, Sep. 15, 1993, abandoned.

[51] Int. Cl.$^6$ .................................................. B32B 15/04
[52] U.S. Cl. .................... 428/469; 428/472; 428/472.3; 428/702
[58] Field of Search ........................... 428/469, 471, 428/472, 472.1, 472.3, 702; 424/601

[56] References Cited

U.S. PATENT DOCUMENTS

| | | | |
|---|---|---|---|
| 4,770,943 | 9/1988 | Hakamatsuka | 428/471 |
| 4,847,163 | 7/1989 | Shimamune | 428/471 |
| 4,871,578 | 10/1989 | Adam et al. | 428/471 |
| 4,960,646 | 10/1990 | Shimamune | 428/471 |

FOREIGN PATENT DOCUMENTS

| | | |
|---|---|---|
| 0 407 698 A1 | 1/1991 | European Pat. Off. |
| 4371146 | 12/1992 | Japan. |

*Primary Examiner*—Timothy Speer
*Attorney, Agent, or Firm*—Choate, Hall & Stewart

[57] ABSTRACT

A process for the production of a hydroxyapatite coated article includes contacting a coating comprising hydroxyapatite with a recrystallization medium, pressurizing the recrystallization medium, heating the coated article under conditions of reduced oxygen activity at a temperature in the range of 100° to 350° C. A process for the production of highly crystalline hydroxyapatite coated articles includes contacting a coating comprising hydroxyapatite with recrystallization medium containing hydroxyapatite particles, pressurizing the recrystallization medium, and heating the immersed coated article under conditions effective to crystallize hydroxyapatite.

5 Claims, 3 Drawing Sheets

HYDROXYAPATITE COATINGS AND A METHOD OF THEIR MANUFACTURE

This is a continuation of application Ser. No. 08/121,792 filed on Sep. 15, 1993 now abandoned.

FIELD OF THE INVENTION

The present invention relates to a process for coating orthopedic and dental implant materials with biocompatible materials. The present invention particularly relates to a process for coating orthopedic and dental implants with highly crystalline calcium phosphate ceramics.

BACKGROUND OF THE INVENTION

Orthopedic and dental implants are commonly coated with a substance to provide a surface suitable for the ingrowth of bone tissue, thereby securely anchoring the implant to the existing bone. The biocompatibility of the coating substance further minimizes implant rejection and increases the useful life of the implant. Calcium phosphate ceramics, such as tricalcium phosphate (TCP) and hydroxyapatite (HA), are particularly suitable materials. Hydroxyapatite is particularly preferred since it is a naturally occurring material in bone.

Hydroxyapatite has been applied to implants using thermal plasma spray techniques. However, hydroxyapatite disadvantageously decomposes into amorphous calcium phosphates during thermal plasma spraying. These decomposition products are more soluble in aqueous and physiological solutions than crystalline hydroxyapatite, and their presence in medical implant coatings (typically as high as 50%) increases the dissolution rate of the coating and can result in premature failure of the implant system.

Earlier attempts have been made to produce more highly crystalline hydroxyapatite coatings. A plasma sprayed coating of tricalcium phosphate (TCP) has been converted to hydroxyapatite by reaction in water at elevated temperature and atmospheric pressure; and a similar TCP coating has been converted to hydroxyapatite by hydrothermal treatment in aqueous calcium phosphate solutions at 80°–200° C. and 0.1–2 MPa. A mixed phase coating derived from plasma sprayed hydroxyapatite and containing amorphous calcium phosphate, tricalcium phosphate, and hydroxyapatite has been converted into hydroxyapatite by a hydrothermal treatment in pure $H_2O$ at 200° C. and 2 MPa.

None of the prior art coating processes have been able to provide a commercial hydroxyapatite coating of crystallinity greater than 90% crystalline hydroxyapatite content. Moreover, high temperature treatment in water/air environments, such as the prior art processes, result in the disadvantageous oxidation of the metallic implant ("tarnish"). Such oxidation can degrade the quality and mechanical integrity of the interface between the coating and the implant.

It is the object of the present invention to provide a hydroxyapatite coating for use on medical implant devices having improved crystallinity over prior art processes and reduced solubility of the hydroxyapatite layer.

It is another object of the present invention to provide a hydroxyapatite coated medical implant device having no disadvantageous oxidation of the metallic implant surface.

SUMMARY OF THE INVENTION

In one aspect of the invention, a process for production of a hydroxyapatite coated article includes contacting an article having a hydroxyapatite coating with a recrystallization medium, the recrystallization medium comprising hydroxyapatite particles and a liquid; pressuring the recrystallization medium; and heating the coated article under conditions sufficient to effect crystallization of the hydroxyapatite coating.

In another aspect of the invention, a process for production of a hydroxyapatite coated article includes contacting an article having a hydroxyapatite coating with a recrystallization medium; pressurizing the recrystallization medium; and heating the coated article to effect crystallization of the hydroxyapatite coating under conditions of reduced oxygen activity. "Reduced oxygen activity", which results in reduced oxidation of a metallic substrate, is defined herein as the reduced tendency of the recrystallization medium to oxidize the article, as compared to a standard oxygen activity. The standard oxygen activity is defined as that oxygen activity of an aqueous recrystallization medium at equilibrium with ambient air. As used herein, atmospheric air is defined to be the conditions found at the reaction site location.

In another aspect of the invention, a process for production of a hydroxyapatite coated article includes contacting an article having a hydroxyapatite coating with a recrystallization medium, the recrystallization medium comprising hydroxyapatite particles; pressurizing the recrystallization medium and heating the coated article to effect crystallization of the hydroxyapatite coating under conditions of reduced oxygen activity.

In yet another aspect of the invention, a process for production of a hydroxyapatite coated article includes contacting an article having a hydroxyapatite coating with a recrystallization medium, the recrystallization medium comprising hydroxyapatite particles in a mixture of an organic liquid and water; pressurizing the recrystallization medium; and heating the coated article under conditions sufficient to effect crystallization of the hydroxyapatite coating.

In preferred embodiments, the recrystallization medium comprises hydroxyapatite particles. The hydroxyapatite particles are preferably 0.01 to 10 wt %, and more preferably 0.5 wt %, of the recrystallization medium. The hydroxyapatite particles are preferably crystalline. The crystal size of the hydroxyapatite is in the range of 1 to 5 microns, although larger sized (up to 200 microns) multi-crystal aggregates may be used.

The liquid of the crystallization medium may be water, an aqueous solution, an organic liquid or mixtures thereof. In other preferred embodiments, the recrystallization medium is preferably a hydroxyapatite suspension in 90% ethanol:10% $H_2O$.

The heat treatment is preferably carried out at a temperature in the range of 100° to 350° C. and, more preferably, in the range of 200° to 300°C. for 1 to 170 h and, more preferably, 1 to 20 h. Pressurization may be internally or externally generated and is preferably in the range of 0.01 to 15 MPa.

In preferred embodiments, reduced oxygen activity may be accomplished by use of an organic liquid in the recrystallization medium, reduced concentration of dissolved oxygen in the recrystallization medium, addition of an oxygen scavenger compound to the recrystallization medium, reduced reaction temperatures or replacement of the atmospheric air with an oxygen diluting atmosphere such as an inert gas or water vapor.

By "oxygen scavenger compound", as that term is used herein, it is meant a compound which has a high affinity for molecular oxygen or which chemically reacts with molecular oxygen to form a compound that does not oxidize the implant material. Oxygen scavenger compounds include alcohols, organic esters, and alkanes.

By "oxygen diluting atmosphere", as that term is used herein, it is meant an atmosphere which is used to displace the normally occurring oxygen of ambient air. The oxygen diluting atmosphere is itself inactive with respect to oxidation.

In another preferred embodiment, a vessel containing the recrystallization medium and coated article is evacuated and an oxygen diluting atmosphere is introduced prior to heating.

In another preferred embodiment, a vessel containing the recrystallization medium and coated article is evacuated and then sealed prior to heating, thereby forming a deoxygenated water vapor atmosphere.

In yet another preferred embodiment, a vessel containing the recrystallization medium and coated article is heated to boil the liquid which comprises the recrystallization medium. Boiling is carried out for 1 to 30 minutes and preferably for 2 to 10 minutes.

In yet another aspect of the invention, a hydroxyapatite coated article contains a metallic substrate and a hydroxyapatite coating of greater than 90% crystalline hydroxyapatite. The exposed metallic surfaces of the article are not oxidized more than that resulting from exposure of the article to atmospheric air. In a preferred embodiment, the exposed metallic surfaces of the article have no oxidation as determined by lack of metal discoloration by visual inspection.

The method of the invention results in the recrystallization of the amorphous and non-hydroxyapatite components of the precursor coatings and the production of a coating containing greater than 90% crystalline hydroxyapatite. The coatings of the invention are substantially less soluble and contain significantly more crystalline hydroxyapatite than conventional coatings and lack the disadvantageous oxidation present in conventionally treated coatings.

BRIEF DESCRIPTION OF THE DRAWINGS

Other features and advantages of the invention will be apparent from the following description with reference to the Drawing, in which.

DESCRIPTION OF THE PREFERRED EMBODIMENT

Figure 1A:
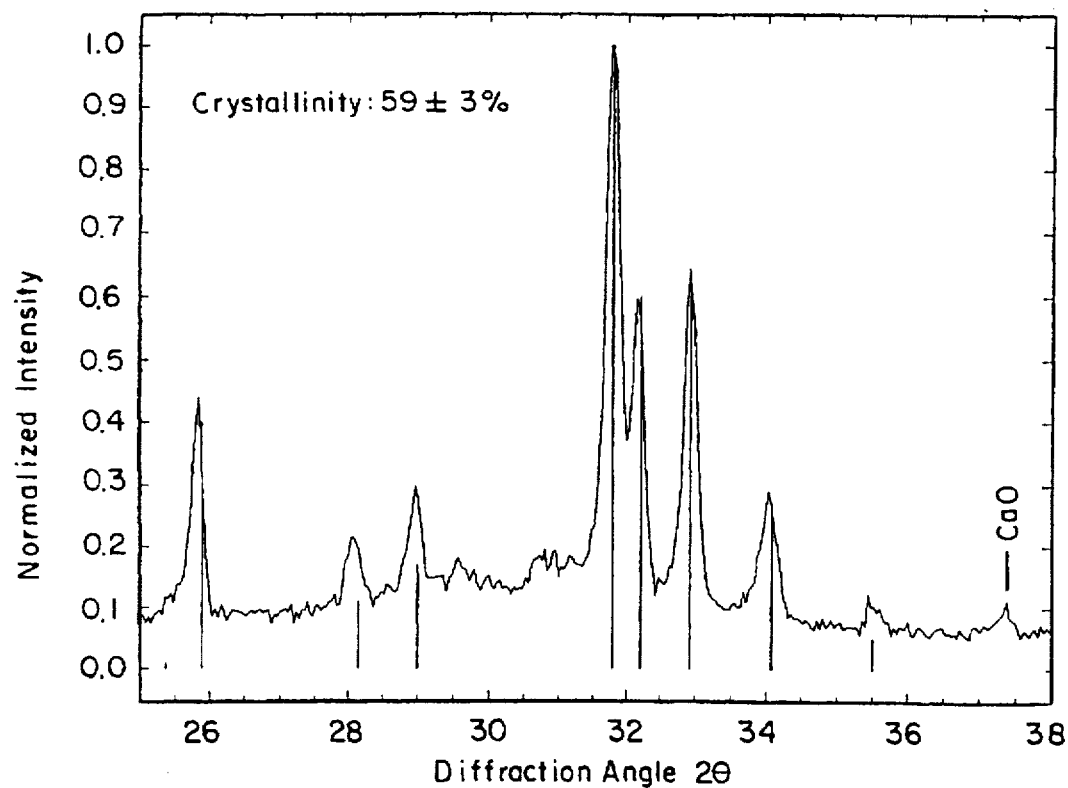
FIG. 1 is x-ray diffraction patterns for hydroxyapatite coatings deposited by commercial thermal plasma spray techniques that are (a) untreated; (b) subjected to the lyothermal treatment of the invention at 250° C.; (c) subjected to the hydrothermal treatment of the invention at 250° C.; and (d) subjected to the hydrothermal treatment of the invention at 125° C.
Figure 1B:
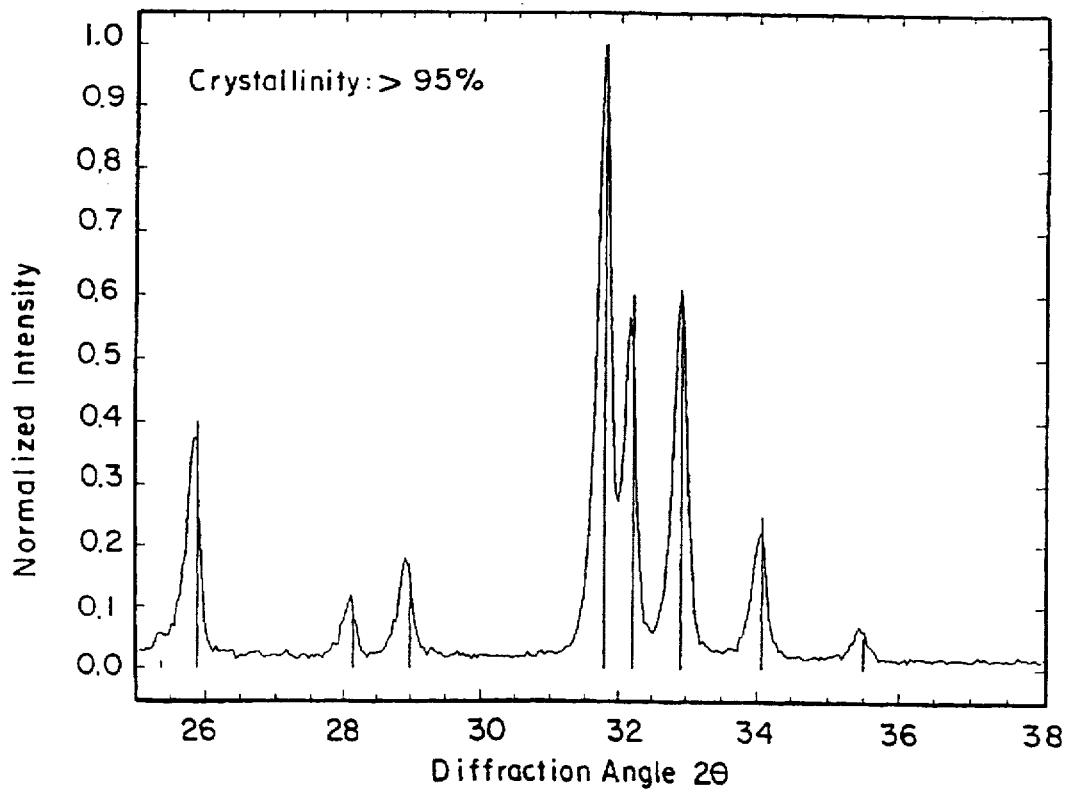
Figure 1C:
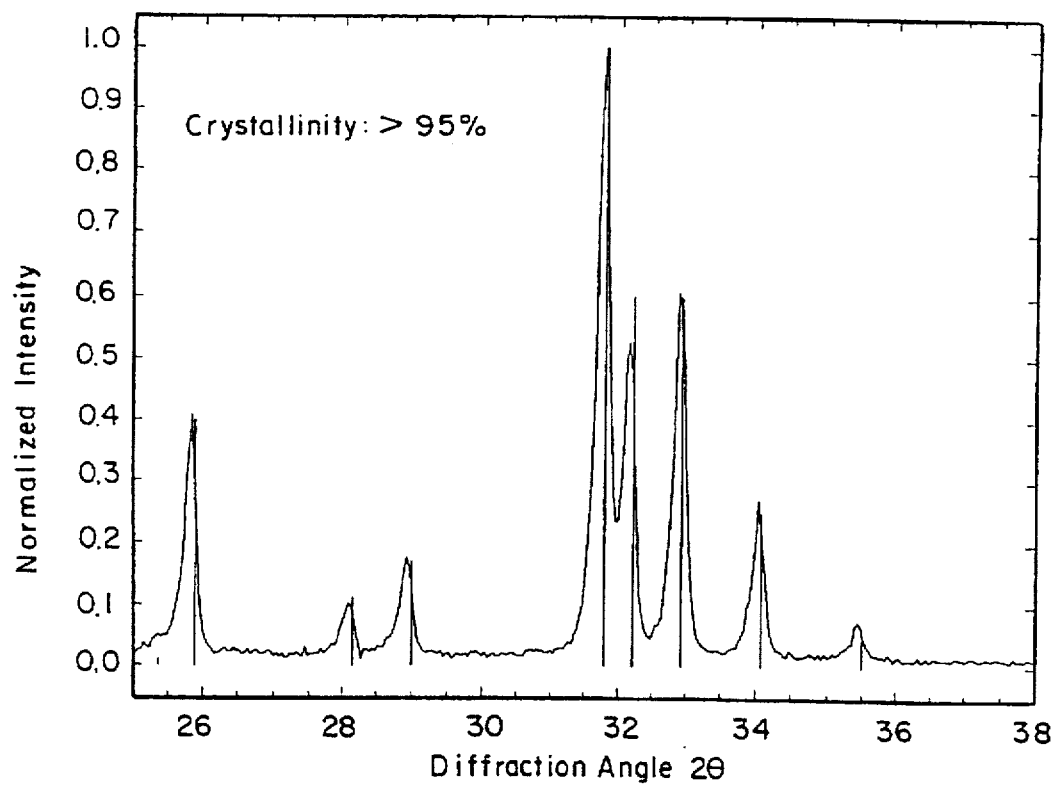
Figure 1D:
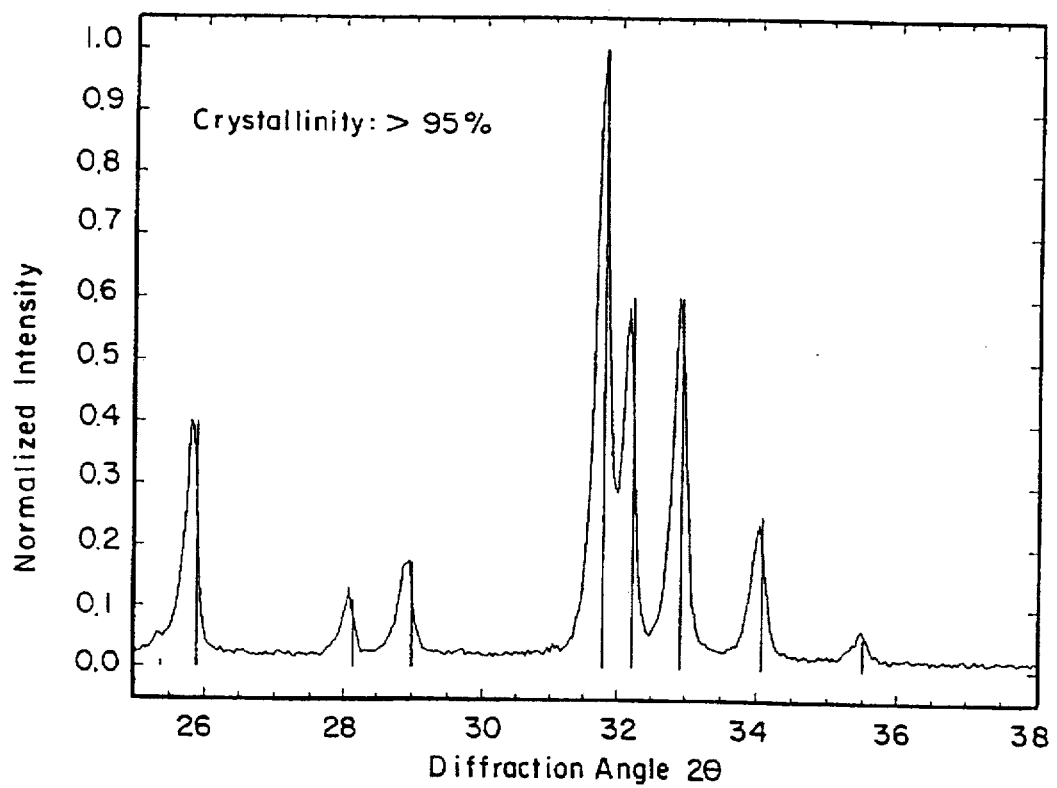

A detailed description of the hydroxyapatite coated article and of the method for its production according to the present invention follows.

Implant bodies suitable for use with the method of the present invention are typically hard, wear-resistant, metallic materials. Suitable metallic materials include, but are in no way limited to, titanium and its alloys with vanadium and aluminum; and chromium/cobalt alloys. An implant body may be coated with hydroxyapatite using conventional thermal plasma spray techniques. Plasma spray coated samples are available from commercial vendors, such as Bio-Coat, Inc., Southfield, Mich. and APS-Materials, Dayton, Ohio. The coatings are prepared according to Federal Drug Administration standards for thermal plasma spray hydroxyapatite coatings on metallic medical devices. Such coatings have a thickness in the range of 25–200 microns and are most typically approximately 50 microns.

Other known deposition techniques are also within the scope of the invention, including electrodeposition, such as described in U.S. Ser. No. 07/828,011 entitled "Electrophoretic Deposition of Calcium Phosphate on Metal Substrates", incorporated herein by reference, and sputter deposition, such as described in U.S. Ser. No. 08/052,150 entitled "Method of Coating Medical Devices and Devices Coated Thereby", incorporated herein by reference.

The present invention has recognized that a highly crystalline hydroxyapatite coating may be obtained in a hydrothermal or lyothermal process when the recrystallization medium contains hydroxyapatite particles. However; high temperature hydrothermal processes typically oxidize exposed metal surfaces resulting in an undesirable oxide "tarnish". The present invention has additionally recognized that in order to prepare hydroxyapatite coated articles without disadvantageous surface oxidation, the hydrothermal or lyothermal treatment is carried out under conditions of reduced oxygen activity.

By "lyothermal", as that term is used herein, it is meant a high pressure and temperature treatment carried out in a wide range of organic solvents. Water may be used in the lyothermal process in conjunction with an organic solvent; however, it is not the primary component of the recrystallization solution.

By "hydrothermal", as that term is used herein, it is meant a high pressure and temperature (above 100° C.) treatment in water or aqueous solution. Where reference is made to reducing oxygen activity, it is understood that such method can be used in conjunction with either the hydrothermal or lyothermal processes as described above.

The hydrothermal treatment of the present invention can provide a highly crystalline hydroxyapatite coating over a range of treatment temperatures and operating times. A "low temperature" hydrothermal treatment of hydroxyapatite coatings according to the present invention includes heating the coated articles in a recrystallization medium containing hydroxyapatite particles at 100° to 125° C. for more than 70 h and provides highly crystalline hydroxyapatite coatings with little of the concomitant oxidation of any exposed substrate.

The hydroxyapatite particles have a particle size in the range of 1 to 5 microns and may be in the form of multi-crystal aggregates up to 200 microns in size. Hydroxyapatite particles are commercially available from Clarkson Chromatography Products, Inc., Williams, Pa. It has been determined with this invention that the presence of hydroxyapatite particles in the recrystallization medium enhances the crystallinity of the resultant coating. It is hypothesized that the particles serve as nucleation sites for conversion of amorphous hydroxyapatite and non-hydroxyapatite into crystalline hydroxyapatite. It is preferred that the hydroxyapatite particles be crystalline.

A "high temperature" hydrothermal treatment includes heating the coated article in a recrystallization medium containing hydroxyapatite particles at 200° to 350° C. for 1 to 20 h. However, without use of conditions of reduced oxygen activity in order to minimize undesirable oxidation of exposed substrate surfaces the coated article is undesirably tarnished.

The lyothermal treatment of hydroxyapatite coatings according to the present invention includes heating the coated article in a mixture of an organic liquid and water at elevated temperatures and pressures and provides highly crystalline hydroxyapatite coatings without the concomitant oxidation of any exposed substrate surface. Both "low temperature" (100°–125° C.) and "high temperature" (200°–350° C.) lyothermal processes are contemplated within the scope of the invention.

The coated article is contacted with a recrystallization medium. As described above, an aqueous recrystallization medium is used in a hydrothermal process and an organic liquid-based recrystallization medium is used in a lyothermal process. The recrystallization medium may be pressurized by external means. External means may include, by way of example and in no way limited to, gas pressurization. Internal pressurization may include, by way of example and in no way limited to, sealing the recrystallization medium in a vessel and heating.

In one embodiment of the invention, the oxidation activity of recrystallization medium is reduced by using an organic liquid as a component of the recrystallization liquid. The organic liquid typically includes alcohols, esters and alkanes which have a high affinity for molecular oxygen or which may react with molecular oxygen to inactivate molecular oxygen. By preferentially interacting with molecular oxygen, the organic liquid effectively reduces the oxygen activity of the molecular oxygen within the reaction vessel. Water is used in the lyothermal process in conjunction with an organic liquid; however, it is not the primary component of the recrystallization medium. Water may be present in the range of 1 to 20% vol. Alcohols are particularly preferred, in particular those which are miscible with water. A particularly preferred recrystallization medium includes 90:10 ethanol:water by volume.

In another embodiment of the present invention, the oxygen activity of the system is reduced by boiling the liquid of the recrystallization medium to drive out dissolved gases. Boiling for 1 to 30 minutes is sufficient. The recrystallization medium and the coated article are then sealed in a vessel before beginning the lyothermal or hydrothermal treatment and a solvent saturated atmosphere is established above the recrystallization medium. Boiling has several advantageous results: (1) vapor replaces air (particularly oxygen), forming a deoxygenated atmosphere above the recrystallization medium; (2) oxygen dissolved in the recrystallization liquid is released, further decreasing the amount of molecular oxygen of the system; (3) carbon dioxide dissolved in the recrystallization liquid is also released. The first two effects result in decreased oxidation of the implant, as described above. The third effect, removal of $CO_2$, is advantageous when treating certain coatings that would otherwise form some carbonate apatite during the lyothermal treatment. Carbonate apatite is undesirable because it is much more soluble than hydroxyapatite.

Oxygen activity may also be reduced in a hydrothermal or lyothermal process by evacuating a vessel holding the recrystallization medium and the coated article and backfilling the vessel with a oxygen diluting atmosphere. The reaction vessel is then sealed. Oxygen diluting atmospheres include, but are not limited to nitrogen, inert gases and deoxygenated solvent vapor. Evacuation of the recrystallization medium provides a deoxygenated atmosphere above the recrystallization medium and removes dissolved gases, further decreasing the amount of dissolved molecular oxygen in the recrystallization liquid.

In a typical process, a titanium or chromium/cobalt alloy implant is coated by a standard thermal plasma spray process. The x-ray diffraction data and solubility data of an untreated hydroxyapatite coating is compared to the hydrothermally and lyothermally treated samples of the present invention.

The crystallinity of treated and untreated coatings can be determined by analysis of x-ray diffraction patterns. The x-ray diffraction pattern of the coatings of FIG. 1 were obtained by illumination of the respective coating with Cu K$\alpha$ radiation. The pattern of the untreated coating is illustrated in FIG. 1(a) and shows low intensity diffraction peaks and a broad hump in the background centered around 30° 2$\theta$, which indicates the presence of a significant amount of amorphous material. A quantitative analysis of the x-ray diffraction data based upon integrated peak intensities (performed by CAMET Research, Inc., Goleta, Calif.) revealed that the coating consisted of approximately 50% crystalline hydroxyapatite, 5% tricalcium phosphate, 1% calcium oxide, and 4% other crystalline materials; the remaining 40% was noncrystalline, amorphous calcium phosphate. Such a composition is typical of untreated plasma sprayed hydroxyapatite.

The solubility of the treated and untreated plasma sprayed hydroxyapatite coatings of FIG. 1 were determined by monitoring the calcium ion concentration of a slowly stirred 0.1M $KH_2PO_4$ buffer solution (pH=4.40) into which the sample had been immersed. In a typical experiment, the hydroxyapatite coating was on a rectangular titanium alloy substrate and had dimensions of 1×1.5×0.2" (2.54×3.81×0.5 cm). The coating thickness was approximately 50 microns; approximately 120 mg of coating was initially present. The experiment was conducted in a 200 ml buffer solution containing 4 ml of 4M KCl (to maintain a standard ionic strength for the calcium ion electrode). The solution was stirred at a constant rate for the duration of the experiment. Calcium ion concentration was continuously monitored and measurements were recorded periodically. Calcium concentration over time for the untreated coating is shown by curve (a) in FIG. 2. The pH increased slightly over the duration of each of the solubility experiments and had an average value of 4.5.

Figure 2:
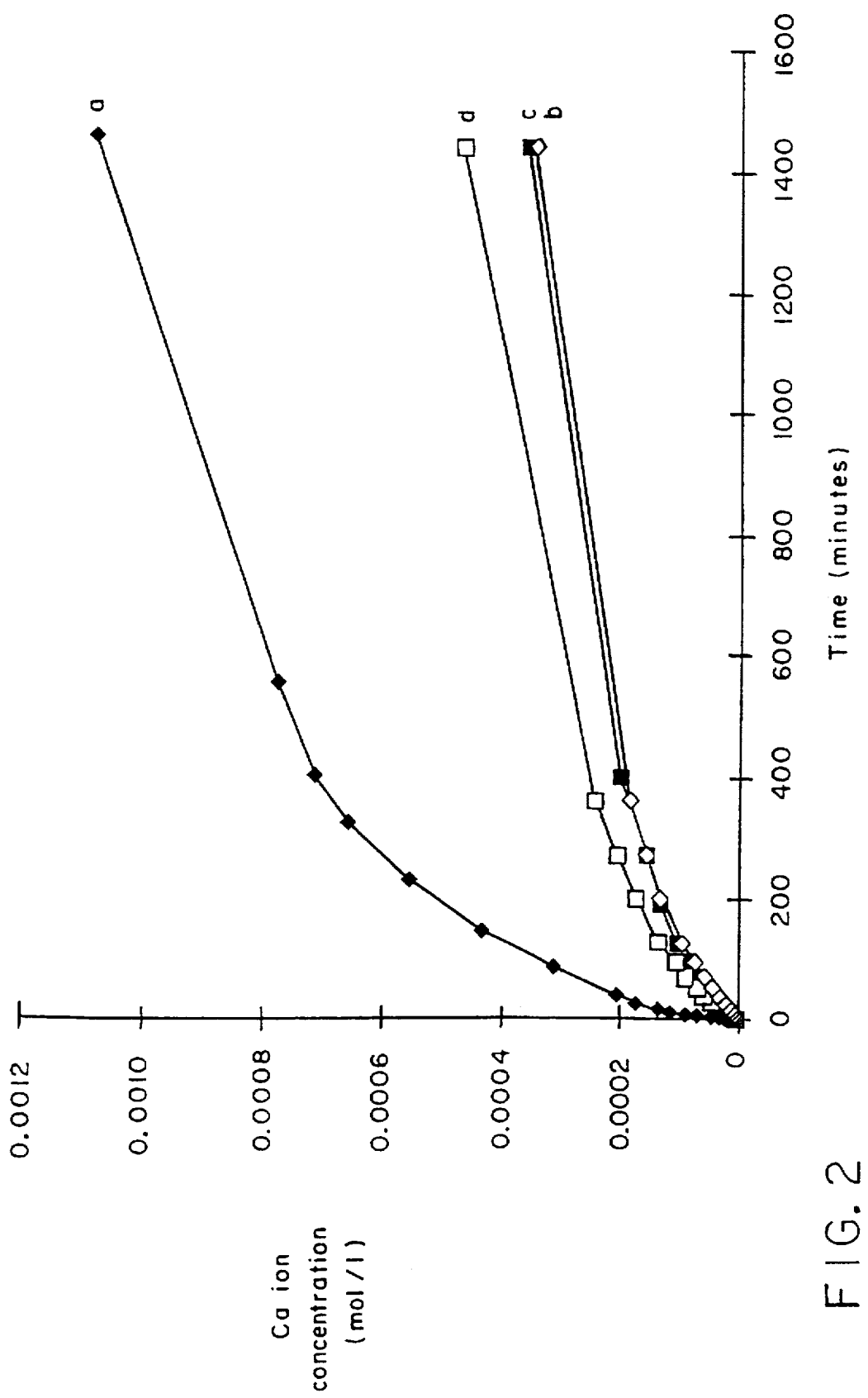
FIG. 2 is a graph of calcium ion concentration versus time for acidic solutions containing an immersed hydroxyapatite coated titanium alloy plate, with curves labeled as in FIG. 1.

The crystallinity and solubility of lyothermally and hydrothermally treated coatings at both "low" temperatures (125° C.) and "high" temperatures (250° C.) are illustrated in FIGS. 1 and 2, (b) through (d). These treatments are performed on coatings identical to the standard spray material shown in FIGS. 1(a) and 2(a).

Treatment B, corresponding to curves (b) in FIGS. 1 and 2, is performed lyothermally by immersing the coating in a recrystallization medium consisting of 90:10 mixture (by volume) of ethanol and water with the addition of 0.5 wt % hydroxyapatite. This hydroxyapatite was a commercially available, high quality, stoichiometric, well-crystallized material with a 1–5 micron crystal size aggregated into 60–120 micron clumps. The hydroxyapatite was dispersed by stirring and allowed to settle to the bottom of the polyfluorethylene-lined reaction vessel. The ethanol serves to reduce the activity of molecular oxygen in the vessel to prevent undesirable oxidation of the metal surface. The vessel was sealed and placed in an oven at 250° C. for a period of 15 hours. The pressure in the vessel was governed by the vapor pressure over the 90:10 ethanol:water mixture, and was approximately 7 MPa.

Treatment C, corresponding to curves (c) in FIGS. 1 and 2, is performed hydrothermally in a recrystallization medium consisting of pure distilled $H_2O$ containing 0.5 wt % of the hydroxyapatite as described above. This sample was held at 250° C. (a "high" temperature) for 15 h at a pressure governed by the vapor pressure of $H_2O$, approximately 3.9 MPa. No attempt was made to reduce molecular oxygen activity within the reaction vessel.

Treatment D, corresponding to curves (d) in FIGS. 1 and 2, is performed hydrothermally in a recrystallization medium consisting of pure $H_2O$ plus 0.5 wt % of the hydroxyapatite as described above. This sample was held at a "low temperature" of 125° C. for 72 h at a pressure governed by the vapor pressure of $H_2O$, approximately 0.23 MPa. The sample required longer treatment time to achieve high crystallinity, because of the reduced temperature; however, the low temperature hydrothermal treatment yields a relatively untarnished metal finish.

The properties of coatings derived from treatments B and C are identical. Both exhibit very high crystallinity and hydroxyapatite content (FIG. 1), in which quantitative analysis yields greater than 95% crystalline hydroxyapatite. This indicates almost complete conversion of the amorphous material and non-hydroxyapatite calcium phosphates to hydroxyapatite. Both exhibit very low solubility, more than a factor of four lower than that exhibited by the standard spray (FIG. 2). However, treatment B showed no noticeable oxidation of the titanium alloy metal as determined by visible observation. In contrast, treatment C resulted in a oxidation of the metal substrate as is clearly visible in the formation of a deep purple, blue, and yellow tarnish on the hydrothermal sample. The sample prepared by treatment D also was highly crystalline, had low solubility and very little tarnish was observed upon visual inspection.

A further consideration for a hydroxyapatite coated article for use as a medical implant is the mechanical strength of the coating. Mechanical tests were performed on coated samples following dissolution experiments of 6 hour duration. The samples were rinsed in distilled $H_2O$ and thoroughly dried and prepared for a lap shear test according the ASTM standard 1044-87. After 6 hours of dissolution, the average failure of untreated plasma spray coatings occurred at 1100±50 psi, while the average failure of the lyothermally and hydrothermally treated samples was 1620±50 psi. This is compared to the average failure of an untreated plasma spray coating prior to dissolution experiments of 1610±30 psi. There were no significant differences in the mechanical integrity of the lyothermally and hydrothermally treated samples.

It has been demonstrated that lyothermal treatments in the presence of a recrystallization medium containing an organic liquid and hydrothermal treatments, all with hydroxyapatite present, result in significantly higher crystalline hydroxyapatite content and lower solubility than standard plasma spray coatings. Moreover, the treatment under conditions of reduced oxygen activity yield an untarnished metallic surface, which is more desirable in medical applications where long term durability of the hydroxyapatite/substrate interface is critical. It has also been demonstrated that low temperature/long term hydrothermal treatments are equally effective with the lyothermal treatment in yielding high crystalline hydroxyapatite content and low solubility hydroxyapatite coatings with little disadvantageous oxidation. The higher temperatures made possible with the lyothermal treatment, however, impart the additional advantage of being effective in short runs (⅕ as long, in the above examples), and are consequently more economical.

The hydroxyapatite-coated article of the present invention is characterized by the greater than 90% crystallinity of the hydroxyapatite coating and the absence of surface oxidation as observed by visual inspection.

Changes and modifications in the specifically described embodiments can be carried out without departing from the scope of the invention which is intended to be limited only by the scope of the claims.

What is claimed is:

1. A hydroxyapatite coated article, comprising a metallic article having an at least 90% crystalline hydroxyapatite coating disposed thereon, and having substantially no oxidation of the metallic article surface, said hydroxyapatite coated article prepared by:

contacting an article, said article having a hydroxyapatite coating, with a recrystallization medium, said recrystallization medium comprised of hydroxyapatite particles and a liquid;

pressurizing said recrystallization medium; and heating the coated article to effect crystallization of said hydroxyapatite coating under conditions of reduced oxygen activity of an aqueous recrystallization medium in equilibrium with atmospheric air.

2. A hydroxyapatite coated article, comprising a metallic article having an at least 90% crystalline hydroxyapatite coating disposed theron, and having substantially no oxidation of the metal article surface, said hydroxyapatite coated article prepared by:

contacting the article, said article having a hydroxyapatite coating, with a recrystallization medium, said recrystallization medium comprising a liquid;

pressurizing said recrystallization medium; and heating the coated article under conditions of reduced oxygen activity, said reduced oxygen activity being less than the oxygen activity of an aqueous recrystallization in equilibrium with atmospheric air.

3. A hydroxyapatite coated article, comprising a metallic article having an at least 90% crystalline hydroxyapatite coating dispersed thereon, and having substantially no oxidation of the metallic article surface said hydroxyapatite coated article prepared by:

contacting the article, said article having a hydroxyapatite coating, with a recrystallization medium, said recrystallization medium comprised of hydroxyapatite particles and a mixture of an organic liquid and water;

pressurizing said recrystallization medium; and heating the coated article under conditions sufficient to effect crystallization of the hydroxyapatite coating.

4. The hydroxyapatite coated article of claim 1, 2 or 3, wherein said metallic article comprises a metal selected from the group consisting of titanium, vanadium, aluminum, chromium, cobalt and alloys thereof.

5. The hydroxyapatite coated article of claim 1, 2 or 3 wherein said hydroxyapatite coating is at least 95% crystalline.

* * * * *